United States Patent [19]

Kurashige et al.

[11] Patent Number: 5,219,744
[45] Date of Patent: Jun. 15, 1993

[54] PROCESS FOR MODIFYING FATS AND OILS

[75] Inventors: Jun Kurashige; Narihide Matsuzaki, both of Kawasaki; Tamio Mase; Shotaro Yamaguchi, both of Nishikasugai, all of Japan

[73] Assignees: Ajinomoto Co., Inc., Tokyo; Amano Pharmaceutical Co., Ltd., Nagoya, both of Japan

[21] Appl. No.: 722,388

[22] Filed: Jun. 26, 1991

Related U.S. Application Data

[63] Continuation of Ser. No. 236,762, Aug. 26, 1988, abandoned.

[30] Foreign Application Priority Data

Aug. 26, 1987 [JP] Japan .................. 62-212390

[51] Int. Cl.$^5$ .................. C12P 7/66; C12P 7/64; C12N 9/16; C12N 9/18
[52] U.S. Cl. .................. 435/135; 435/134; 435/136; 435/196; 435/197; 435/198; 435/933
[58] Field of Search ............. 435/134, 135, 136, 196, 435/197, 198, 933

[56] References Cited

U.S. PATENT DOCUMENTS

| | | | |
|---|---|---|---|
| 4,275,011 | 6/1981 | Tanaka et al. | 435/134 |
| 4,275,081 | 6/1981 | Coleman et al. | 426/33 |
| 4,416,991 | 11/1983 | Matsuo et al. | 435/134 |
| 4,472,503 | 9/1984 | Matsuo et al. | 435/176 |

FOREIGN PATENT DOCUMENTS

| | | | |
|---|---|---|---|
| 62-00287 | 1/1987 | Japan . | |
| 239990 | 10/1987 | Japan | 435/933 |
| 63-12599 | 3/1988 | Japan . | |

OTHER PUBLICATIONS

Iwai et al, *Agr. Biol. Chem.* vol. 39 (5) pp. 1063–1070 1975.
ATCC Catalogue of Fungi, 1989, pp. 243–244.

*Primary Examiner*—Douglas W. Robinson
*Assistant Examiner*—L. Blaine Lankford
*Attorney, Agent, or Firm*—Oblon, Spivak, McClelland, Maier & Neustadt

[57] ABSTRACT

A process for modifying fats and oils which comprises applying partial glyceride lipase to fats and oils containing partial glycerides and fatty acids to synthesize triglycerides from the partial glycerides by esterification.

The lipase is preferably an immobilized lipase and this process is preferably carried out under a water concentration of 1500 ppm or less.

By using partial glyceride lipase according to the present invention, there can be obtained modified fats and oils having a low content of diglycerides without changing triglyceride composition.

9 Claims, No Drawings

PROCESS FOR MODIFYING FATS AND OILS

This application is a continuation of application Ser. No. 07/236,762, filed on Aug. 26, 1988, now abandoned.

BACKGROUND OF THE INVENTION

1. Field of the Invention

The present invention relates to a process for modifying fats and oils with an enzyme, and more specifically relates to a process for modifying fats and oils which comprises applying partial glyceride lipase (lipase which does not act on triglycerides but acts on diglycerides and/or monoglycerides is referred to as partial glyceride lipase in the present application) to fats and oils containing partial glycerides (whereby diglycerides and monoglycerides are referred to) to synthesize triglycerides from the included partial glycerides by esterification without changing the fatty acid composition of triglycerides (hereinafter referred to as triglyceride composition) in the fats and oils.

Namely, the present invention aims to obtain in a high yield fats and oils containing triglycerides in high content by esterifying partial glycerides which are impurities contained in the fats and oils without change in the triglyceride composition.

2. Description of the Prior Art

Fats and oils contain triglycerides as main components, and monoglycerides and diglycerides, which are partial glycerides, free fatty acids, etc. as additional components.

The above partial glycerides and free fatty acids are those formed by enzymatical or non-enzymatical hydrolysis during storage, oil extraction and/or purification. The free acids and monoglycerides can be removed by known methods such as alkali deacidification and steam distillation, but no effective industrial separating method for diglycerides has been found.

Recently, a method has been reported wherein oils of high triglycerides content are obtained by synthesizing triglycerides from diglycerides by esterification using a triglyceride lipase. However, transesterification progresses together with ester synthesis in these reaction, and it is intrinsically impossible to avoid change in triglyceride composition.

Further, a method has been reported as a method for removal of diglycerides using an enzyme wherein only diglycerides are selectively hydrolyzed with partial glyceride lipase (Japanese Patent Unexamined Published Application (hereinafter referred to as "J. P. KOKAI") No. 62-287). This method is excellent in that the enzyme has almost no reactivity with triglycerides and thus high triglyceride content oil can be obtained.

However, some difficulties follows when this method is industrially practiced. First of all, yield is lowered as a natural result of carrying out hydrolysis. Further, it is necessary to separate glycerol which is a hydrolyzate, from the reaction solution. Further, as for the fatty acids which are hydrolyzates, their concentration are high and thus purification yield is extremely lowered under adoption of conventional alkali deacidification. Therefore, it is compelled to utilize physical deacidification, namely steam distillation, which, however, causes a problem that hydrolysis autocatalytically progresses owing to high temperature treatment under high fatty acid concentration to result in lowering of yield and formation of diglycerides. For these problems, it is still difficult to industrially practice this method, and a better method is now desired.

Diglycerides whose separation is difficult as above mentioned cause problems, for example, that (1) they interfere with the formation of crystal nuclei of triglycerides and lower crystallization rate of triglycerides, (2) they inhibit transition rate into stable crystal shape, namely crystal transition, of triglycerides, (3) they makes fractionation of triglycerides difficult based on action of lowering SFC (solid fat content) and (4) they promote rise of acid value when used as fry oil.

A method for solving these problems wherein triglycerides are synthesized from diglycerides by esterification using conventional triglyceride lipase changes triglyceride composition by transesterification which simultaneously takes place and as a result gives an oil having changed various physical properties, and therefore cannot be applied when change in triglyceride composition would be avoided.

Further, a method of removing diglyceride by hydrolysis using partial glyceride lipase has a problem in purification and yield.

SUMMARY OF THE INVENTION

An object of the invention is to provide a method free from the above problems for preparation of fats and oils having low content of diglycerides in low cost and high yield without changing triglyceride composition.

As a result of vigorous study for solving the above problems, the present inventors have found that by making partial glyceride lipase act on fats and oils containing diglycerides, monoglycerides and fatty acids under low water content, the diglycerides and the fatty acids can readily be converted to triglycerides, and moreover triglyceride composition of the thus obtained high triglyceride content fats and oils does not change as compared with the starting fats and oils, and have completed the present invention.

That is, the present invention provides a process for modification of fats and oils which comprises making only ester synthesis progress using partial glyceride lipase without accompanying transesterification to obtain fats and oils of low diglyceride content in high yield. According to the present process, fatty acids contained in the starting material are also converted to triglycerides by ester synthesis, and thus purification load and purification loss of triglycerides are also greatly reduced.

DETAILED DESCRIPTION OF THE INVENTION

Partial glyceride lipases used in the invention are enzymes which on the one hand have a property to hydrolyze so-called monoglycerides wherein one of three hydroxyl groups of glycerol has been esterified with a fatty acid and/or so-called diglycerides wherein hydroxyl groups of 1- and 2-positions (or 2- and 3-positions) or 1- and 3-positions of glycerol have been esterified with fatty acids, but on the other hand have almost nil reactivity with triglycerides wherein all of the three positions have been esterified.

Partial glyceride lipases usable in the present invention include, for example, monoglyceride lipases derived from animal internal organs such as rat intestine and porcine fat tissue, and lipases having specificity to monoglycerides and diglycerides as produced by filamentous fungi of the genus Penicillium. Preferably used are lipases derived from a strain of the genus Penicillium, particularly partial glyceride lipase produced by *Penicillium cyclopium* which is deposited with American Type Culture Collection, 12301 Parklawn Drive, Rockville, Md., 20852, U.S.A. under the accession number of ATCC 34613. There can be mentioned Lipase G (manufactured by Amano Seiyaku Co, Ltd.) as an example of commercially available partial glyceride lipase used in the present invention.

So-called triglyceride lipases having a high reactivity with not only partial glycerides but also triglycerides cannot be used in the present invention because they make not only ester synthesis but also ester interchange progress at the same time and thus make fatty acid composition of triglycerides different from that of the starting fats and oils whereby various properties change.

Animal and vegetable fats and oils generally have different fatty acid distribution at the 1-, 2- and 3-positions owing to mechanism of triglyceride synthesis in vivo. Therefore, when triglyceride lipase is applied to the fats and oils, fatty acid composition of triglycerides changes. More in detail, triglyceride lipases include enzymes having no position specificity to the three positions of glycerol and enzymes exhibiting specificity only to the 1- and 3-positions. Use of the former type enzymes causes utterly random distribution of fatty acids binding to the three positions as is the case in chemical ester interchange, and use of latter type enzymes causes standarization of the 1- and 3-positions, and thus in either case compositions of the resulting triglycerides changes from those of the starting triglycerides.

It has been known that partial glyceride lipases used in the present invention exhibit activity only on partial glycerides, and it has already been reported that partial glycerides in fats and oils are removed by hydrolysis using this property (J. P. KOKAI No. 62-287).

However, no preceding literature has been known which indicates the fact or suggests the possibility that such partial glyceride lipase is capable of synthesizing triglyceride on which the enzyme intrinsically does not exhibit enzymatic activity, from diglycerides by esterification.

Ester synthesis of triglycerides from diglycerides in the present invention is a reaction intrinsically different from hydrolysis of diglycerides. This is because both reactions are different in substrate and do not stand in a relation of reversible reaction with each other as shown below DG+H$_2$O⇌2FFA+Glycerol [hydrolysis of DG]

DG+FFA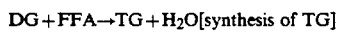→TG+H$_2$O [synthesis of TG]

(DG: Diglyceride FFF: Free Fatty Acid TG: Triglyceride)

In other words, the present invention has been accomplished based on the discovery of the new fact that partial glyceride lipase catalyzes ester synthesis reaction alone among two reversible reactions of ester synthesis and hydrolysis of diglycerides and triglycerides, and does not substantially catalyze ester interchange and hydrolysis of triglycerides.

Fats and oils used in the invention are fats and oils containing much partial glycerides, i.e. monoglycerides and diglycerides, for example, palm oil, rice oil, corn oil and olive oil. There can of course be used fats and oils other than the above mentioned ones, for example, liquid fats such as rapeseed oil, safflower oil and soybean oil and solid fats such as lard, tallow and beef kennen fat. There can further be used fats and oils obtained by processing the above fats and oils, for example by subjecting them to treatment such as fractionation, hydrogenation or ester interchange.

According to necessity, fatty acids may be added alone or in combination of two or more of them to the above fats and oils. Amount of fatty acids to be added is not particularly limited. However, when too much fatty acids are added, purification of fats and oils after the enzymatic reaction becomes difficult and yield is lowered. Therefore, it is usually preferable to add fatty acids in an amount of 0.5 to 10 times the molar amount of; diglycerides present in the starting fats and oils. Kind of fatty acids to be added is not particularly limited, and there may be added any of saturated fatty acids such as palmictic acid and stearic acid and unsaturated fatty acids such as oleic acid and linoleic acid.

As for the reaction conditions of the present invention, partial glyceride lipase is applied under the condition for ester synthesis, and thus it is preferable to use a reaction system wherein water can be removed as perfect as possible. Since the enzymatic activity is hard to display under low water content, it is usually preferable to use enzyme immobilized on an immobilizing carrier. There can be used as an immobilizing carrier any of adsorption type carriers such as Celite, clay, cellulose and its derivatives, chitosan and its derivatives and ion exchange resins; and entrapment type carriers such as photohardening resins and sodium alginate. A weight ratio of an enzyme to a carrier is preferably between 1: 4 and 1: 400.

In order to enhance display of enzymatic activity under the conditions in the present invention, it is preferable to coexist an enzyme activator such as a surfactant such as sucrose fatty acid esters, lecithin, sorbitan fatty acid esters and polyglycerin fatty acid esters; sugars such as glucose, fructose, galactose, sucrose, maltose, cellobiose, lactose, raffinose, stachiose and dextrin; and polyalcohols such as sorbitol, erythritol, ethylene glycol, in preparation of immobilized enzymes, as is indicated in Japanese Patent Application No. 63-33009. Proper amount of the enzyme activator to be added is usually 10 to 500 weight percent based on the enzyme weight.

Amount of the immobilized enzyme to be added to fats and oils is not particularly limited, but may usually be 2 to 30 weight % based on the weight of the starting fats and oils.

Reaction temperature can appropriately be selected according to the optimum temperature of immobilized partial glyceride lipase to be used and the melting point of fats and oils to be used, and is usually preferably 20° to 80° C.

As for water content, the partial glyceride lipase catalyzes hydrolysis of diglycerides and synthetic reaction to triglycerides, as is described above, and when water content is high, the enzyme catalyzes hydrolysis. Therefore, a condition under which water is removed as perfect as possible is necessary in the present invention. Although the water concentration changes depending on concentration of diglycerides and fatty acids in fats and oils to be used in the reaction, it is usually preferable to adjust the water content of the reaction system to 1 to 1500 ppm, preferably 10 to 200 ppm.

Removal of water can be carried out by distillation under reduced pressure, use of a dehydrating agent such as molecular sieve, use of inert dry gas such as nitrogen gas, etc.

Any of batch reaction; continuous reaction using a bioreactor in a column method, a fluidized bed method or the like is applied as reaction mode, wherein the enzyme can effectively be utilized.

Although the desired object can fully be attained without any solvent under the condition of the present invention, an organic solvent may be added according to necessity. Any organic solvent can be used as such organic solvent so long as it does not inhibit the activity of partial glyceride lipase and can dissolve fats and oils, and include, for example, n-hexane, octane, petroleum ether, diethyl ether, acetone or ethyl acetate.

By using partial glyceride lipase according to the present invention, there can be obtained modified fats and oils having a low content of diglycerides without changing triglyceride composition.

Thus obtained modified fats and oils have allow content of fatty acids, monoglycerides and diglycerides, and thus purification yield is high and purification cost is low.

Further, the modified fats and oils having a low diglyceride content exhibits a rapid crystallization rate, is hard to undergo hydrolysis and has an unchanged triglyceride composition and therefore, there can be expected enlargement of use thereof in wide range including salad oil, fry oil and the like.

Now, the present invention is further illustrated by the following non-limitative representative examples.

EXAMPLE 1

Lipase G (manufactured by Amano Seiyaku Co., Ltd.) (200 mg) originated from *Penicillium cyclopium* ATCC 34613 as partial glyceride lipase and 100 mg of commercially available powdery lecithin were dissolved in 2 g of water. The solution was uniformly sprayed on 2 g of Celite to carry out immobilization, and the resulting product was dried under reduced pressure of 15 mmHg at 40° C. to remove unnecessary water. The thus obtained immobilized enzyme (2 g) was added to 20 g of crude palm olein oil containing 8.7% diglycerides and 0.3% monoglycerides (total 9.0% as partial glycerides) and 5.2% fatty acids, and shaking reaction was carried out at 60° C. In this connection, 8 g of Molecular Sieves 3A was added at the same time as a dehydrating agent. After the reaction, the resulting fats and oils were separated from the immobilized enzyme and molecular sieves, and subjected to gas chromatography to analyze its composition. The results are shown in Table 1. Water content of the fats and oils measured by the Karl Fisher method was 42 ppm, 35 ppm and 32 ppm at 24, 48 and 72 hours after the reaction, respectively. It was also clarified from the result that ester synthesis progressed without changing the triglyceride composition.

TABLE 1

| Reaction time (hrs) | FFA (%) | MG (%) | DG (%) | TG (%) | Fatty acid composition of TG (%) | | | | |
|---|---|---|---|---|---|---|---|---|---|
| | | | | | C46 | C48 | C50 | C52 | C54 |
| Starting material | 5.2 | 0.3 | 8.7 | 85.8 | 0.3 | 3.0 | 41.4 | 45.0 | 10.3 |
| 24 | 3.9 | 0.1 | 7.0 | 89.0 | 0.3 | 3.1 | 40.1 | 45.1 | 11.4 |
| 48 | 2.8 | 0.1 | 4.8 | 92.4 | 0.4 | 3.6 | 39.2 | 44.8 | 12.0 |
| 72 | 2.1 | 0.1 | 3.2 | 94.6 | 0.5 | 4.2 | 38.7 | 44.6 | 12.0 |

FFA: fatty acid MG: monoglyceride
DG: diglyceride TG: triglyceride
C46 to C54 indicate total carbon number of fatty acids of triglycerides

EXAMPLE 2

In order to confirm the addition effect of lecithin (a surfactant) two kinds of immobilized enzymes were prepared by adding no lecithin or adding lecithin in an amount of 5% of Celite in immobilization of 10% (based on the weight of Celite) a enzyme (Lipase G) with Celite, and examined for their effect. Reaction conditions such as amount of the enzyme agent and the molecular sieve to be added to the fats and oils, and temperature were similar to those in Example 1, and reaction time was 48 hours. As is shown in Table 2, it was recognized that although the enzyme exhibited a synthetic activity without addition of lecithin, the activity was increased twice or three times by addition of lecithin. Water content measured after the reaction was 38 ppm in either case.

TABLE 2

| | FFA (%) | MG (%) | DG (%) | TG (%) | Fatty acid composition of TG (%) | | | | |
|---|---|---|---|---|---|---|---|---|---|
| | | | | | C46 | C48 | C50 | C52 | C54 |
| No addition of lecithin | 3.2 | 0.1 | 6.5 | 90.2 | 0.4 | 3.4 | 39.9 | 45.0 | 11.3 |
| Addition of lecithin | 2.4 | 0.1 | 4.1 | 93.4 | 0.4 | 3.9 | 38.6 | 44.6 | 12.5 |
| Composition of starting fats and oils | 5.2 | 0.3 | 8.7 | 85.8 | 0.3 | 3.0 | 41.4 | 45.0 | 10.3 |

EXAMPLE 3

Changes of fatty acid composition of triglycerides were compared after the reaction using Lipase G as a partial glyceride lipase, and three kinds of triglyceride lipase, i.e., Lipase P originated from *Pseudomonas fluorescens*, Lipase D originated from *Rhizopus delemer* and Lipase F-AP originated from *Rhizopus javanicus*.

Among the triglyceride lipases, Lipase P is a representative example of enzymes having no position specificity to triglycerides and Lipase D and Lipase F-AP originated from the strains of the genus Rhizopus are representative examples of enzymes having specificity to the 1- and 3-positions of triglycerides.

Immobilization on Celite was carried out by dissolving 200 mg of each enzyme together with 100 mg of lecithin in 2 g of water and spraying on 2 g of Celite, and drying under reduced pressure was successively carried out. Reaction was carried out in a manner similar to that in Example 1, and the resulting triglycerides were measured for their fatty acid composition by gas chromatography 48 hours thereafter. The results are shown in Table 3.

Further, water contents after the reaction were 35 ppm in Lipase G, 29 ppm in Lipase P, 38 ppm in Lipase D and 32 ppm in Lipase F-AP.

TABLE 3

| Enzyme | Glyceride specificity | TG position specificity | Fatty acid composition of TG (%) | | | | |
|---|---|---|---|---|---|---|---|
| | | | C46 | C48 | C50 | C50 | C54 |
| Lipase G | Partial glycerides | — | 0.4 | 3.6 | 39.2 | 44.8 | 12.0 |
| Lipase P | Triglycerides | None | 1.2 | 10.3 | 32.8 | 39.4 | 16.3 |
| Lipase D | Triglycerides | 1,3-position | 0.9 | 6.7 | 35.5 | 42.3 | 14.6 |
| Lipase F-AP | Triglycerides | " | 1.0 | 7.1 | 34.3 | 42.2 | 15.4 |
| Starting fats and oils | | | 0.3 | 3.0 | 41.4 | 45.0 | 10.3 |

It is seen from the results of Table 3 that since a small amount of triglycerides synthesized from diglycerides were contained in the resulting triglycerides in use of Lipase G as partial glyceride lipase, a small change in the composition was recognized as compared with the starting fats and oils. However, the change was very small as compared with the cases in use of the triglyceride lipases, and it would arise no substantial problems.

EXAMPLE 4

A immobilized enzyme (prepared by immobilizing 17.4 g of Lipase G and 8.7 g of lecithin to 174 g of Celite in a manner similar to that in Example 1) (200 g) was added to 1,000 g of crude palm olein oil having the composition consisting of 86.2% triglycerides, 5.0% fatty acids, 0.3% monoglycerides and 8.5% diglycerides, and the mixture was subjected to reaction with stirring under reduced pressure of 1.0 mmHg at 60° C. for 48 hours. Water concentration at the time was 25 ppm. After completion of the reaction, the fats and oils were collected by filtration and the fats and oils adhered to the enzyme agent were collected using n-hexane. The thus obtained reacted fats and oils weighed 996 g.

Further, in order to remove the fatty acids from the above reacted fats and oils, physical deacidification was carried out by conventional steam distillation to 972 g of product (yield 97.2%). This yield is higher than conventional purification yield of palm oil, and much higher as compared with partial glyceride-removing method by hydrolysis. The results are indicated in Table 4.

TABLE 4

| | Weight (g) | FFA (%) | MG (%) | DG (%) | TG (%) | Fatty acid composition of TG (%) | | | | |
|---|---|---|---|---|---|---|---|---|---|---|
| | | | | | | C46 | C48 | C50 | C52 | C54 |
| Starting oil | 1,000 | 5.0 | 0.3 | 8.5 | 86.2 | 0.3 | 3.0 | 41.3 | 45.0 | 10.4 |
| Reaction oil | 996 | 1.4 | 0.1 | 2.0 | 96.5 | 0.5 | 4.2 | 38.5 | 44.4 | 12.4 |
| Purified oil | 972 | 0.0 | 0.0 | 2.1 | 97.9 | 0.5 | 4.1 | 38.5 | 44.5 | 12.4 |

EXAMPLE 5

Lipase G (manufactured by Amano Seiyaku Co., Ltd.) (100 mg) as a partial glyceride lipase and 200 mg of sucrose (guaranteed reagent, manufactured by Junsei Kagaku Co., Ltd.) were dissolved in 500 mg of water. The resulting solution was mixed with 5 g of Celite (No. 535, manufactured by Manville Co.) to prepare an immobilized lipase agent.

The immobilized lipase (2 g) (water content about 10%) was packed in a column having the inner diameter of 1 cm and the length of 10 cm. A starting oil (crude palm olein oil, TG content 87.3%, DG content 7.7%) whose water content had been adjusted to 8 ppm was quantitatively run with a pump. After 3 hrs run, reaction oil at the column outlet was returned to the column inlet through the dehydrating column (having the inner diameter of 2.4 cm and the length of 29 cm and being packed with Molecular Sieves No. 3A) at the flow rate of 10 g/h. The reaction system was maintained at 55° C. Water content, TG and DG contents and TG composition at the column outlet measured after 5 hours recycle are shown in Table 5. Table 5 shows that the outlet TG content slightly increased and the outlet DG content decreased, which demonstrates that the synthetic reaction progressed without a significant change in TG composition.

TABLE 5

| | | Reaction oil after 5 hrs recycle | Starting material |
|---|---|---|---|
| Water concentration at the column outlet (ppm) | | 48 | 8 |
| Glyceride content at the column outlet (%) | TG | 87.6 | 87.3 |
| | DG | 4.9 | 7.7 |
| Fatty acid composition of TG at the column outlet (%) | C46 | 0.3 | 0.3 |
| | C48 | 3.2 | 2.9 |
| | C50 | 41.0 | 41.6 |
| | C52 | 45.0 | 44.7 |
| | C54 | 10.5 | 10.4 |

What is claimed is:

1. A process for modifying fats and oils, which comprises:
    applying partial glyceride lipase produced by *Penicillium cyclopium* ATCC 34613 to fats and oils containing partial glycerides and fatty acids and having a total water concentration of 1 to 1500 ppm; and
    synthesizing triglycerides by esterifying said partial glycerides with said fatty acids wherein the esterification is promoted by said partial glyceride lipase, thereby modifying said fats and oils without interesterification.

2. The process of claim 1 wherein the fats and oils are selected from the group consisting of palm oil, rice oil, corn oil, olive oil, rapeseed oil, safflower oil, soybean oil, lard, tallow, beef kennen fat and their processed products.

3. The process of claim 1 wherein the partial glyceride lipase is immobilized on an immobilizing carrier.

4. The process of claim 3 wherein the immobilizing carrier is a conventional adsorption type carrier or entrapment type carrier.

5. The process of claim 3 wherein amount of the immobilized lipase to be added to the fats and oils is 2 to 30 weight % based on the weight of the fats and oils.

6. The process of claim 3 wherein the immobilization is carried out in the presence of an enzyme activator.

7. The process of claim 6 wherein the enzyme activator is selected from the group consisting of a sucrose fatty acid ester, lecithin, a sorbitan fatty acid ester, a polyglycerin fatty acid ester, glucose, fructose, galactose, sucrose, maltose, cellobiose, lactose, raffinose, stachiose, dextrin, sorbitol, erythritol and ethyleneglycol.

8. The process of claim 6 wherein an amount of the enzyme activator to be added is 10 to 50 weight % based on the weight of the enzyme.

9. The process of claim 1 wherein the reaction temperature is selected from a temperature range of between 20° to 80° C.

* * * * *